US011783931B2

(12) United States Patent
Spotts et al.

(10) Patent No.: US 11,783,931 B2
(45) Date of Patent: *Oct. 10, 2023

(54) DRUG MONITORING TOOL

(71) Applicant: TAKEDA PHARMACEUTICAL COMPANY LIMITED, Osaka (JP)

(72) Inventors: Gerald Spotts, Lexington, MA (US); Roman Pichler, Lexington, MA (US); Michael Nelson, Lexington, MA (US)

(73) Assignee: TAKEDA PHARMACEUTICAL COMPANY LIMITED, Osaka (JP)

( * ) Notice: Subject to any disclaimer, the term of this patent is extended or adjusted under 35 U.S.C. 154(b) by 157 days.

This patent is subject to a terminal disclaimer.

(21) Appl. No.: 17/119,011

(22) Filed: Dec. 11, 2020

(65) Prior Publication Data
US 2021/0098103 A1    Apr. 1, 2021

Related U.S. Application Data

(63) Continuation of application No. 15/876,827, filed on Jan. 22, 2018, now Pat. No. 10,896,749.
(Continued)

(51) Int. Cl.
*G16H 20/10* (2018.01)
*G16C 20/30* (2019.01)
(Continued)

(52) U.S. Cl.
CPC .............. *G16H 20/10* (2018.01); *G06N 7/01* (2023.01); *G09C 5/00* (2013.01); *G16C 20/30* (2019.02);
(Continued)

(58) Field of Classification Search
CPC ........ G16H 10/00; G16H 10/60; G16H 20/00; G16H 20/10; G16H 50/30; G16H 50/00; G16H 50/50; G16B 40/00; G16B 50/00
(Continued)

(56) References Cited

U.S. PATENT DOCUMENTS 4,709,331 A    11/1987   Barkett et al.
4,807,170 A     2/1989   Kulli et al.
(Continued)

FOREIGN PATENT DOCUMENTS

CN    101035579 A    9/2007
EP     0737926 A1   10/1996
(Continued)

OTHER PUBLICATIONS

Ryman, Josiah Thomas; The Development of Methods to Account for Physiologic Dynamic Changes and Their Effects on the Pharmacokinetics of Therapeutic Monoclonal Antibodies and Other Therapeutics; The University of Tennessee Health Science Center. ProQuest Dissertations Publishing, 2017.10263404. (Year: 2017).*
(Continued)

*Primary Examiner* — Hiep V Nguyen
(74) *Attorney, Agent, or Firm* — TROUTMAN PEPPER HAMILTON SANDERS LLP

(57) ABSTRACT

A drug monitoring tool comprises a data receiver and an interactive user interface. The data receiver is configured to receive a pharmacokinetic (PK) profile of a patient. The interactive user interface is configured to display, to the patient, a time-varying therapeutic plasma protein level of the patient and delineate a plurality of zones within the interactive user interface associated with the time-varying therapeutic plasma protein level. The plurality of zones includes a safe zone indicating to the patient that the time-varying therapeutic plasma protein level is within a first concentration range considered safe for physical activity and a danger zone indicating to the patient that the time-varying therapeutic plasma protein level is within a second concentration range and physical activity should be limited.

6 Claims, 5 Drawing Sheets

Related U.S. Application Data

(60) Provisional application No. 62/451,391, filed on Jan. 27, 2017.

(51) Int. Cl.
| | | |
|---|---|---|
| *G09C 5/00* | (2006.01) | |
| *G16H 50/30* | (2018.01) | |
| *G16H 50/50* | (2018.01) | |
| *G06N 7/01* | (2023.01) | |
| *G16H 10/60* | (2018.01) | |
| *H04L 9/06* | (2006.01) | |
| *G16B 50/00* | (2019.01) | |
| *G16B 40/00* | (2019.01) | |
| *G16C 20/90* | (2019.01) | |

(52) U.S. Cl.
CPC ............. *G16H 10/60* (2018.01); *G16H 50/30* (2018.01); *G16H 50/50* (2018.01); *H04L 9/0637* (2013.01); *G16B 40/00* (2019.02); *G16B 50/00* (2019.02); *G16C 20/90* (2019.02)

(58) Field of Classification Search
USPC .......................................................... 705/2
See application file for complete search history.

(56) References Cited

U.S. PATENT DOCUMENTS

| | | | |
|---|---|---|---|
| 4,810,243 | A | 3/1989 | Howson |
| 4,898,578 | A | 2/1990 | Rubalcaba, Jr. |
| 5,104,374 | A | 4/1992 | Bishko et al. |
| 5,326,545 | A | 7/1994 | Koksbang |
| 5,462,222 | A | 10/1995 | Boeck, II |
| 5,508,202 | A | 4/1996 | Enomoto et al. |
| 5,522,798 | A | 6/1996 | Johnson et al. |
| 5,609,575 | A | 3/1997 | Larson et al. |
| 5,630,664 | A | 5/1997 | Farrelly |
| 5,678,571 | A | 10/1997 | Brown |
| 5,681,285 | A | 10/1997 | Ford et al. |
| 5,770,384 | A | 6/1998 | Androphy et al. |
| 5,789,160 | A | 8/1998 | Eaton et al. |
| 5,897,493 | A | 4/1999 | Brown |
| 5,915,971 | A | 6/1999 | Ramsay et al. |
| 6,093,392 | A | 7/2000 | High et al. |
| 6,099,837 | A | 8/2000 | Turecek et al. |
| 6,167,412 | A | 12/2000 | Simons |
| 6,188,570 | B1 | 2/2001 | Borkowski |
| 6,317,719 | B1 | 11/2001 | Schrier et al. |
| 6,321,164 | B1 | 11/2001 | Braun et al. |
| 6,330,426 | B2 | 12/2001 | Brown et al. |
| 6,381,577 | B1 | 4/2002 | Brown |
| 6,421,650 | B1 | 7/2002 | Goetz et al. |
| 6,489,289 | B2 | 12/2002 | Nortersheuser et al. |
| 6,542,858 | B1 | 4/2003 | Grass et al. |
| 6,564,153 | B2 | 5/2003 | Braun et al. |
| 6,647,358 | B2 | 11/2003 | Grass et al. |
| 6,658,396 | B1 | 12/2003 | Tang et al. |
| 6,747,002 | B2 | 6/2004 | Cheung et al. |
| 6,790,668 | B1 | 9/2004 | Ferreira et al. |
| 6,944,638 | B1 | 9/2005 | Putnam |
| 6,978,286 | B2 | 12/2005 | Francis et al. |
| 7,043,415 | B1 | 5/2006 | Dunlavey et al. |
| 7,204,823 | B2 | 4/2007 | Estes et al. |
| 7,229,430 | B2 | 6/2007 | Hickle et al. |
| 7,693,697 | B2 | 4/2010 | Westenskow et al. |
| 7,813,880 | B2 | 10/2010 | Vaidya et al. |
| 7,837,647 | B2 | 11/2010 | Estes et al. |
| 7,860,583 | B2 | 12/2010 | Condurso et al. |
| 7,862,506 | B2 | 1/2011 | Brown |
| 7,867,165 | B2 | 1/2011 | Brown |
| 7,869,852 | B2 | 1/2011 | Brown |
| 7,871,376 | B2 | 1/2011 | Brown |
| 7,875,288 | B2 | 1/2011 | Balu-Iyer et al. |
| 7,972,267 | B2 | 7/2011 | Brown |
| 7,990,251 | B1 | 8/2011 | Ford, Jr. |
| 7,997,269 | B2 | 8/2011 | Yudkovitch et al. |
| 7,998,734 | B2 | 8/2011 | High et al. |
| 8,046,242 | B1 | 10/2011 | daCosta et al. |
| 8,156,158 | B2 | 4/2012 | Rolls et al. |
| 8,197,437 | B2 | 6/2012 | Kalefut et al. |
| 8,321,148 | B2 | 11/2012 | Lockhart et al. |
| 8,326,649 | B2 | 12/2012 | Rosenfeld |
| 8,380,539 | B2 | 2/2013 | Linder et al. |
| 8,412,538 | B2 | 4/2013 | Hardaway |
| 8,449,884 | B2 | 5/2013 | Rivera et al. |
| 8,540,664 | B2 | 9/2013 | Robertson et al. |
| 8,546,096 | B2 | 10/2013 | Dockal et al. |
| 8,560,337 | B2 | 10/2013 | Schneider et al. |
| 8,574,856 | B2 | 11/2013 | Selinfreund et al. |
| 8,589,175 | B2 | 11/2013 | Glauser et al. |
| 8,589,186 | B1 | 11/2013 | Nadas et al. |
| 8,606,526 | B1 | 12/2013 | Fernandez et al. |
| 8,616,895 | B2 | 12/2013 | Brown |
| 8,630,722 | B2 | 1/2014 | Condurso et al. |
| 8,637,320 | B2 | 1/2014 | Schubert et al. |
| 8,644,754 | B2 | 2/2014 | Brown |
| 8,655,259 | B2 | 2/2014 | Brown et al. |
| 8,679,014 | B2 | 3/2014 | Bennett et al. |
| 8,682,687 | B2 | 3/2014 | Hyde et al. |
| 8,744,828 | B2 | 6/2014 | Albisser et al. |
| 8,761,906 | B2 | 6/2014 | Condurso et al. |
| 8,969,524 | B2 | 3/2015 | Steinitz et al. |
| 9,050,318 | B2 | 6/2015 | Dumont et al. |
| 9,061,038 | B2 | 6/2015 | Garland et al. |
| 9,119,918 | B2 | 9/2015 | Robertson et al. |
| 9,142,144 | B2 | 9/2015 | Meglan et al. |
| 9,241,978 | B2 | 1/2016 | Dumont et al. |
| 9,249,209 | B2 | 2/2016 | Cho et al. |
| 9,272,021 | B2 | 3/2016 | Scheiflinger et al. |
| 9,307,907 | B2 | 4/2016 | Condurso et al. |
| 9,340,792 | B2 | 5/2016 | Klaenhammer et al. |
| 9,358,361 | B2 | 6/2016 | Hyde et al. |
| 9,398,863 | B2 | 7/2016 | Viertio-Oja |
| 9,452,108 | B2 | 9/2016 | Ariagno et al. |
| 9,500,639 | B2 | 11/2016 | Dayel et al. |
| 9,512,198 | B2 | 12/2016 | Steinitz et al. |
| 9,572,511 | B2 | 2/2017 | Kochba et al. |
| 9,585,671 | B2 | 3/2017 | Hen et al. |
| 9,603,860 | B2 | 3/2017 | Perrin et al. |
| 9,788,798 | B2 | 10/2017 | Van Ooijen et al. |
| 2001/0001144 | A1 | 5/2001 | Kapp |
| 2001/0041964 | A1 | 11/2001 | Grass et al. |
| 2002/0010595 | A1 | 1/2002 | Kapp |
| 2002/0019706 | A1 | 2/2002 | Braun et al. |
| 2002/0130779 | A1 | 9/2002 | Ford |
| 2003/0023461 | A1 | 1/2003 | Quintanilla et al. |
| 2003/0050225 | A1 | 3/2003 | Butenas et al. |
| 2003/0078760 | A1 | 4/2003 | Bachman et al. |
| 2004/0023211 | A1 | 2/2004 | Groen et al. |
| 2004/0193019 | A1 | 9/2004 | Wei |
| 2005/0008580 | A1 | 1/2005 | Gong et al. |
| 2005/0054942 | A1 | 3/2005 | Melker et al. |
| 2005/0075627 | A1 | 4/2005 | Ward |
| 2005/0130236 | A1 | 6/2005 | Goldman |
| 2005/0147618 | A1 | 7/2005 | Rivera et al. |
| 2005/0165221 | A1 | 7/2005 | Booth et al. |
| 2006/0015261 | A1 | 1/2006 | Mann et al. |
| 2006/0047538 | A1 | 3/2006 | Condurso et al. |
| 2006/0078897 | A1 | 4/2006 | Wedinger et al. |
| 2006/0128624 | A1 | 6/2006 | Cheung et al. |
| 2006/0129357 | A1 | 6/2006 | Francis et al. |
| 2006/0161408 | A1 | 7/2006 | Bachman et al. |
| 2006/0271405 | A1 | 11/2006 | Cipolle et al. |
| 2007/0061393 | A1 | 3/2007 | Moore |
| 2007/0067148 | A1 | 3/2007 | Fritzson et al. |
| 2007/0106536 | A1 | 5/2007 | Moore |
| 2007/0106750 | A1 | 5/2007 | Moore |
| 2007/0106753 | A1 | 5/2007 | Moore |
| 2007/0167853 | A1 | 7/2007 | Melker et al. |
| 2007/0196479 | A1 | 8/2007 | Willmann et al. |
| 2008/0008991 | A1 | 1/2008 | Groen et al. |
| 2008/0033661 | A1 | 2/2008 | Syroid et al. |
| 2008/0040151 | A1 | 2/2008 | Moore |

(56) References Cited

U.S. PATENT DOCUMENTS

| | | |
|---|---|---|
| 2008/0051460 A1 | 2/2008 | Hobden et al. |
| 2008/0052317 A1 | 2/2008 | Francis et al. |
| 2008/0091083 A1 | 4/2008 | Yudkovitch et al. |
| 2008/0091084 A1 | 4/2008 | Yudkovitch et al. |
| 2008/0103824 A1 | 5/2008 | Francis et al. |
| 2008/0108942 A1 | 5/2008 | Brister et al. |
| 2008/0213222 A1 | 9/2008 | High et al. |
| 2009/0006061 A1 | 1/2009 | Thukral et al. |
| 2009/0006133 A1 | 1/2009 | Weinert et al. |
| 2009/0144082 A1 | 6/2009 | Selbst et al. |
| 2009/0144089 A1 | 6/2009 | Heywood et al. |
| 2009/0306944 A1 | 12/2009 | Willmann et al. |
| 2009/0327175 A1 | 12/2009 | He et al. |
| 2010/0036676 A1 | 2/2010 | Safdi et al. |
| 2010/0121185 A1 | 5/2010 | Hyde et al. |
| 2010/0124536 A1 | 5/2010 | Schaub et al. |
| 2010/0143326 A1 | 6/2010 | Rischel et al. |
| 2010/0152545 A1 | 6/2010 | Ramsay et al. |
| 2010/0152620 A1 | 6/2010 | Ramsay et al. |
| 2010/0169063 A1 | 7/2010 | Yudkovitch et al. |
| 2010/0205001 A1 | 8/2010 | Knudsen et al. |
| 2010/0273738 A1 | 10/2010 | Valcke et al. |
| 2010/0312578 A1 | 12/2010 | Hardaway |
| 2011/0015939 A1 | 1/2011 | Lara Gonzalez |
| 2011/0040481 A1 | 2/2011 | Trombley et al. |
| 2011/0060578 A1 | 3/2011 | Ward et al. |
| 2011/0077963 A1 | 3/2011 | Knudsen et al. |
| 2011/0110921 A1 | 5/2011 | Dockal et al. |
| 2011/0145936 A1 | 6/2011 | Ostertag et al. |
| 2011/0184379 A1 | 7/2011 | Van Antwerp et al. |
| 2011/0263690 A1 | 10/2011 | High et al. |
| 2011/0295341 A1 | 12/2011 | Estes et al. |
| 2012/0022497 A1 | 1/2012 | Brown |
| 2012/0041414 A1 | 2/2012 | Estes et al. |
| 2012/0041415 A1 | 2/2012 | Estes et al. |
| 2012/0045742 A1 | 2/2012 | Meglan et al. |
| 2012/0150748 A1 | 6/2012 | Law et al. |
| 2012/0150750 A1 | 6/2012 | Law et al. |
| 2012/0158424 A1 | 6/2012 | Knudsen et al. |
| 2012/0232517 A1 | 9/2012 | Saiki |
| 2012/0316116 A1 | 12/2012 | Scheiflinger et al. |
| 2013/0085712 A1 | 4/2013 | Wang et al. |
| 2013/0085772 A1 | 4/2013 | Gaweda et al. |
| 2013/0108629 A1 | 5/2013 | Dumont et al. |
| 2013/0273047 A1 | 10/2013 | Rivera et al. |
| 2013/0296823 A1 | 11/2013 | Melker et al. |
| 2014/0005501 A1 | 1/2014 | Schabbach et al. |
| 2014/0050717 A1 | 2/2014 | Dockal et al. |
| 2014/0100829 A1 | 4/2014 | Mould |
| 2014/0114676 A1 | 4/2014 | Holmes |
| 2014/0142979 A1 | 5/2014 | Mitsunaga |
| 2014/0232889 A1 | 8/2014 | King et al. |
| 2014/0303901 A1 | 10/2014 | Sadeh |
| 2014/0379629 A1* | 12/2014 | Loew-Baselli ........ G16B 40/20 706/52 |
| 2015/0032470 A1 | 1/2015 | Knudsen et al. |
| 2015/0044207 A1 | 2/2015 | Rivera et al. |
| 2015/0052623 A1 | 2/2015 | Crawford |
| 2015/0053711 A1 | 2/2015 | Ariagno et al. |
| 2015/0185235 A1 | 7/2015 | Sommer |
| 2015/0266944 A1 | 9/2015 | Jiang et al. |
| 2015/0288682 A1 | 10/2015 | Bisroev et al. |
| 2015/0356252 A1 | 12/2015 | Beker |
| 2016/0033523 A1 | 2/2016 | Cameron et al. |
| 2016/0151015 A1 | 6/2016 | Condurso et al. |
| 2016/0174534 A1 | 6/2016 | Ostertag et al. |
| 2016/0184403 A1 | 6/2016 | Scheiflinger et al. |
| 2016/0210436 A1 | 7/2016 | Ambrose et al. |
| 2016/0260003 A1* | 9/2016 | Hill ........................ H04L 9/0894 |
| 2016/0296607 A1 | 10/2016 | Jiang |
| 2016/0300037 A1 | 10/2016 | Mould |
| 2016/0306945 A1 | 10/2016 | Jiang |
| 2016/0335473 A1 | 11/2016 | Pamelard et al. |
| 2016/0346365 A1 | 12/2016 | Pierce et al. |

FOREIGN PATENT DOCUMENTS

| | | |
|---|---|---|
| JP | 2006-155071 A | 6/2006 |
| WO | 2000/15178 A2 | 3/2000 |
| WO | 2002/023186 A2 | 3/2002 |
| WO | 2003/082096 A1 | 10/2003 |
| WO | 2004/070994 A2 | 8/2004 |
| WO | 2005/038049 A2 | 4/2005 |
| WO | 2012/079576 A1 | 6/2012 |
| WO | 2012/160161 A1 | 11/2012 |
| WO | 2012/166795 A1 | 12/2012 |
| WO | 2013/052318 A1 | 4/2013 |
| WO | 2014/063108 A1 | 4/2014 |
| WO | 2014/070953 A1 | 5/2014 |
| WO | WO-2014121257 A1 * | 8/2014 ......... G06F 19/3456 |
| WO | 2015/006033 A1 | 1/2015 |
| WO | 2015085276 A | 6/2015 |
| WO | WO-2015085276 A1 * | 6/2015 ............. A61K 38/37 |
| WO | 2017/180807 A1 | 10/2017 |

OTHER PUBLICATIONS

Ryman Rosiah Thomas; The Development of Methods to Account for Physiologic Dynamic Changes and Their Effects on the Pharmacokinetics of Therapeutic Monoclonal Antibodies and Other Therapeutics; The University of Tennessee Health Science Center. ProQuest Dissertations Publishing, 2017. 10263404. (Year: 2017).*

Examination Report issued with corresponding Australian Patent Application No. 2018213055 dated Feb. 2, 2022.

Bjorkman et al., Pharmacokinetics and dose requirements of factor VIII over the age range 3-74 years, journal, 26 Jun. 2, 2009, pp. 989-998, vol. 65, No. 10, European Journal of Clinical Pharmacology, Berlin, Germany.

Official Action issued in corresponding Eurasian Patent Application No. 201991778 dated Jun. 17, 2020, with informal English translation.

Lanao, Pharmacokinetic basis for the use of extended interval dosage regimens of gentamicin in neonates, journal, May 18, 2004, pp. 193-198, vol. 54, No. 1, Journal of Antimicrobial Chemotherapy, United Kingdom.

Ahnstrom, 2004, A 6-year follow-up of dosing, coagulation factor levels and bleedings in relation to joint status in the prophylactic treatment of haemophilia, Haemophilia 10:689-697.

Bjorkman, 2003, Prophylactic dosing of factor VIII and factor IX from a clinical pharmacokinetic perspective, Haemophilia 9(Suppl 1):101-108.

Bjorkman, 2010, Limited blood sampling for pharmacokinetic dose tailoring of FVIII in the prophylactic treatment of haemophilia A, Haemophilia 16:597-605.

Bjorkman, 2012, Population pharmacokinetics of recombinant factor VIII: the relationships of pharmacokinetics to age and body weight, Blood 119:612-618.

Carlsson, 1993, Pharmacokinetic dosing in prophylactic treatment of hemophilia A, Eur J Haematology 51:247-52.

Collins, 2010, Factor VIII requirement to maintain a target plasma level in the prophylactic treatment of severe iemophilia A: Influences of variance in pharmacokinetics and treatment regimens, J Thrombosis and Haemostasis 8:269-275.

Collins, 2011, Implications of coagulation factor VIII and IX pharmacokinetics in the prophylactic treatment of iaemophilia, Haemophilia 17:2-10.

Duffull, 1997, Comparison of two Bayesian approaches to dose-individualization for once-daily aminoglycoside egimens, B J Clin Pharmacol 43(2):125-35.

Jelliffe, 1993, Individualizing drug dosage regimens: roles of population pharmacokinetic and dynamic models, Bayesian fitting, and adaptive control, Therapeutic Drug Monitoring 15:380-393.

Ljung, 2009, Prophylactic therapy in haemophilia, Blood Reviews 23:267-274.

Lunn, 2005, Bayesian Analysis of Population Pharmacokinetic/Pharmacodynamic Models. in Probabilistic Modeling in Bioinformatics and Medical Informatics, Husmeier et al., Eds_ pp. 351-370 (London).

(56) References Cited

OTHER PUBLICATIONS

McMmichael, 1993, An intelligent and cost-effective computer dosing system for individualizing FK506 therapy in transplantation and autoimmune disorders, J Clin Pharmacol 33:599-605.
Mondorf, 2009, Haemoassist—a hand-held electronic patient diary for haemophilia home care, Haemophilia 15:464-472.
Sherif, 2016, Ptotocols for Secure Electronic Commerce, 3rd Edition.
Office Action issued with corresponding Chinese Patent Application No. 201880014363.7 dated Nov. 14, 2022 (including English Translation).
Written Opinion issued with corresponding Singapore Patent Application No. 11201906837P dated Jul. 6, 2022.

* cited by examiner

DRUG MONITORING TOOL

CROSS REFERENCE TO RELATED APPLICATIONS

This application is a continuation of, and claims priority under 35 U.S.C. § 120 to, U.S. patent application Ser. No. 15/876,827, filed on Jan. 22, 2018, which claims benefit to U.S. Provisional Application No. 62/451,391, filed on Jan. 27, 2017. The entire contents of these applications are incorporated by reference herein in their entirety.

BACKGROUND

Clotting factor VIII is a blood-clotting protein that is activated in response to an injury or bleed. Individuals with relatively low levels of clotting factor VIII are susceptible to internal or external episodes of prolonged bleeding resulting from an injury and/or spontaneous bleeding without a cause. While skin bleeds are not serious, internal bleeding of joints, muscles, and organs can cause permanent damage, disfigurement, or even death.

Patients with hemophilia A have a genetic deficiency that causes low levels of clotting factor VIII. The amount of clotting factor VIII in a patient is expressed as a percentage relative to a normal level. Patients with 5 to 40% of clotting factor VIII are considered to have a mild form of hemophilia A while patients with 1 to 5% of clotting factor VIII are considered to have a moderate form of hemophilia A. Patients with less than 1% of clotting factor VIII are considered to have a severe form of hemophilia A.

Treatment of patients with hemophilia A (or patients that otherwise have low levels of clotting factor VIII) includes providing these patients with periodic infusions of a clotting factor concentrate (e.g., therapeutic plasma protein). The clotting factor concentrate acts as a replacement or supplement for the patient's natural occurring clotting factor VIII. One example of such a therapeutic plasma protein is Shire's ADVATE drug. In some instances, patients receive the therapeutic plasma protein in response to having an uncontrolled internal bleed. Alternatively, patients may be prescribed a prophylactic treatment regimen of the therapeutic plasma protein to reduce the possibility of future bleeds. To avoid any chance of a patient falling below a predetermined threshold, many healthcare providers design treatment regimens that require patients to receive a therapeutic plasma protein infusion every one, two, three, or more days. Currently, patients are provided with electronic diaries to record infusion events. Unfortunately, such diaries do not provide actionable data from which a patient is able to plan activity levels. For example, with current systems, patients are unable to ascertain a risk of bleeding if the patient were to participate in an activity such as playing soccer at any point in time after an infusion event. In particular, with current electronic diaries, patients cannot determine their factor level at any given point in time after a prophylactic infusion event, significantly limiting the usefulness of the information provided by such sources.

SUMMARY

Embodiments of the present disclosure provide a drug monitoring tool that enables a patient to view a personalized, real-time indication of clotting factor VIII levels following a prophylactic infusion event. Advantageously, the disclosed drug monitoring tool allows a patient to significantly reduce bleeding events. For instance, the real-time indication of clotting factor VIII provided by the drug monitoring tool enables the patient to make informed decisions related to an amount and/or intensity of physical activity at any given point in time. In an example in which the drug monitoring tool provides an indication of a low level of clotting factor VIII, the patient may refrain from participating in a physically demanding activity such as a sport, decide to self-administer a non-prophylactic dose of clotting factor VIII in order to participate in the physically demanding activity, or choose a low bleed risk activity (e.g., a stationary activity such as reading a book) until the next prophylactic infusion. Thus, the drug monitoring tool advantageously eliminates patient bleed events due to a lack of actionable information.

In one embodiment, a drug monitoring tool comprises a data receiver configured to receive a pharmacokinetic (PK) profile of a patient. The tool also comprises an interactive user interface configured to present to a patient a time-varying drug concentration level in the patient. The time-varying drug concentration level is based on an administered dose of a subject drug and the PK profile of the patient.

In another embodiment, disclosed is a drug monitoring tool. The tool comprises a data receiver configured to receive a pharmacokinetic (PK) profile of a patient. In addition, the tool comprises an interactive user interface configured to display to the patient a time-varying therapeutic plasma protein level of the patient. The time-varying therapeutic plasma protein level is based on an administered dose of a clotting factor VIII and the PK profile of the patient.

In one aspect of an embodiment, the PK profile of the patient can be based on a Bayesian model of PK profiles of sampled patients and based upon at least one of a bodyweight, von Willebrand factor ("vWF") level, and/or an age of the patient.

In another aspect, the data receiver can be a camera configured to scan a quick response (QR) code storing patient information that includes at least PK profile information. Additionally, the drug monitoring tool can further comprise a QR code processor configured to extract and process the patient information stored within the QR code.

In some aspects, the data receiver can be a communications interface configured to receive the PK profile from a secured server. In this aspect, the received PK profile can be encrypted and the communications interface can be further configured to decrypt the encrypted PK profile.

The drug monitoring tool, in other example embodiments, can further comprise a 20 QR code generator configured to generate the QR code having patient information encrypted using AES-256 encryption with cipher block chaining (CBC) and public-key cryptography standards (PKCS) padding. The QR code generator can be located at a secured server remote from the drug monitoring tool.

The QR code can include at least one of or any combination of: patient identifying information, patient physiological data, patient dosing information, and/or PK profile information of the patient. The patient dosing information can include a prophylactic dosing regimen for a particular clotting factor VIII drug In another aspect, the drug monitoring tool can further comprise an activation toolkit configured to enable access to functionalities of the drug monitoring tool in response to at least one of: receiving the PK profile the patient and/or receiving a log of a first prophylactic infusion of the clotting factor VIII.

In other aspects, the interactive user interface can be configured to display a graphical representation of a time-varying amount of the therapeutic plasma protein within the patient at any given time. The graphical representation can delineate zones associated with the time varying amount of the therapeutic plasma protein. Each zone can be associated with a particular concentration range of the time-varying amount of the therapeutic plasma protein within the patient.

The interactive user interface can also include a graphical control element configured to receive patient input corresponding to a request for the time-varying amount of the therapeutic plasma protein within the patient at a particular time. The interactive user interface can be further configured to display the graphical representation of the time varying amount of the therapeutic plasma protein within the patient at the particular time.

A further embodiment includes a method for drug monitoring executed by a drug monitoring tool. The method includes receiving a pharmacokinetic (PK) profile of a patient. In addition, the method includes enabling an interactive user interface to display to a patient a time—varying therapeutic plasma protein level of the patient. The time-varying therapeutic plasma protein level is based on an administered dose of a clotting factor VIII and the PK profile of the patient.

In one aspect of an embodiment, the PK profile of the patient can be based on a Bayesian model of PK profiles of sampled patients and based upon at least one of a bodyweight, von Willebrand factor ("vWF") level, and/or an age of the patient.

In another aspect, the method can include scanning a quick response (QR) code storing patient information that includes at least PK profile information. In addition, the method can include extracting and processing the patient information stored within the QR code.

In other aspects, the method can include receiving the PK profile from a secured server. The received PK profile can be encrypted. Accordingly, the method can also include decrypting the encrypted PK profile.

In additional aspects, the method can include generating the QR code to have patient information encrypted using AES-256 encryption with cipher block chaining (CBC) and public-key cryptography standards (PKCS) padding.

In certain aspects, the QR code includes at least one of or any combination of: patient identifying information, patient physiological data, patient dosing information, and/or PK profile information of the patient. The patient dosing information can include a prophylactic dosing regimen for a particular clotting factor VIII drug.

Also, the method can include enabling patient access to functionalities of the drug monitoring tool in response to at least of: receiving the PK profile the patient and/or receiving a log of a first prophylactic infusion.

In further aspects, the method can include displaying a graphical representation of a time-varying amount of the therapeutic plasma protein within the patient at any given time. The graphical representation delineates zones associated with the time varying amount of the therapeutic plasma protein. Each zone is associated with a particular concentration range of the time-varying amount of the therapeutic plasma protein within the patient.

Another embodiment of the present disclosure includes a drug monitoring system. The drug monitoring system comprises a therapeutic plasma protein dosing regimen apparatus and a drug monitoring tool.

The therapeutic plasma protein dosing regimen apparatus comprises a model generator configured to create a Bayesian model of pharmacokinetic (PK) profiles of sampled patients. The Bayesian model includes (i) a therapeutic plasma protein clearance and (ii) a volume of distribution relationship for a therapeutic plasma protein based upon at least one of patient age or body weight. The therapeutic plasma protein dosing regimen apparatus also comprises a PK server. The PK server is configured to determine an approximate PK profile of a patient based upon the Bayesian model, a half-life of the therapeutic plasma protein within the patient, and at least one of an age of the patient or a weight of the patient. The PK server is also configured to determine the therapeutic plasma protein dosing regimen including a dosage and a therapeutic plasma protein level over a time period based upon the approximate PK profile of the patient, modify the therapeutic plasma protein dosing regimen in response to receiving a dosing interval for applying a dosage to the patient, and transmit the modified therapeutic plasma protein dosing regimen to the client device.

The drug monitoring tool comprises a data receiver configured to receive the pharmacokinetic (PK) profile of a patient. In addition, the drug monitoring tool comprises an interactive user interface configured to display to the patient a time-varying therapeutic plasma protein level of the patient. The time-varying therapeutic plasma protein level is based on an administered dose of a clotting factor VIII and the PK profile of the patient.

BRIEF DESCRIPTION OF THE DRAWINGS

The foregoing will be apparent from the following more particular description of example embodiments of the disclosure, as illustrated in the accompanying drawings in which like reference characters refer to the same parts throughout the different views. The drawings are not necessarily to scale, emphasis instead being placed upon illustrating embodiments of the present disclosure.

DETAILED DESCRIPTION

Figure 1:
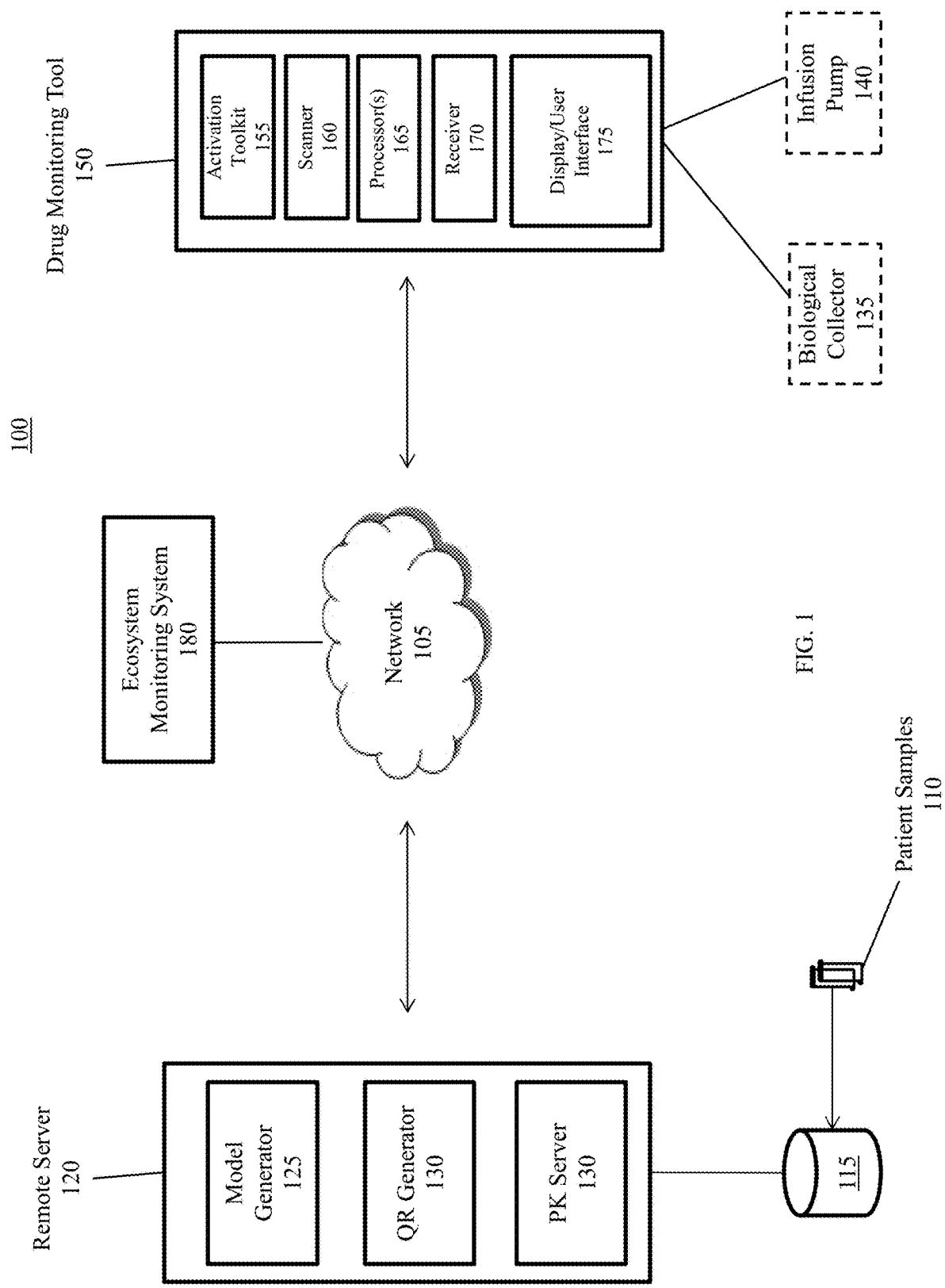
FIG. 1 illustrates an example pharmacokinetic (PK) environment in which a drug monitoring tool operates, according to an example embodiment of the present disclosure.

A description of example embodiments of the present disclosure follows.

The present disclosure relates a drug monitoring tool that enables a patient to view a personalized, real-time indication of clotting factor VIII levels following a prophylactic infusion event. For example, the drug monitoring tool includes a factor meter that enables a user to determine a real-time level of clotting factor VIII. Armed with such information, patients would be better equipped, for example, to determine whether or not they should participate in a physically demanding activity (e.g., a sport such as soccer). Accordingly, the drug monitoring tool enables patients to make informed decisions with respect to their activity levels based on accurate information of their clotting factor VIII levels. In addition, the factor meter provided by the drug monitoring tool enables patients to determine a time-varying amount of clotting factor VIII in their system at any given time after a prophylactic infusion event. Advantageously, patients are then able to plan activity levels in the future based on predicted clotting factor VIII levels.

As used herein, the term "clotting factor VIII", "FVIII", or "rAHF" refers to any FVIII molecule that has at least a portion of the B domain intact, and which exhibits biological activity that is associated with native FVIII. In one embodiment of the disclosure, the FVIII molecule is full-length FVIII. The FVIII molecule is a protein that is encoded by DNA sequences capable of hybridizing to DNA encoding FVIII:C. Such a protein may contain amino acid deletions at various sites between or within the domains A1-A2-B-A3-C1-C2. The FVIII molecule may also be an analog of native clotting factor FVIII, wherein one or more amino acid residues have been replaced by site-directed mutagenesis.

The term "recombinant Factor VIII" (rFVIII) may include any rFVIII, heterologous or naturally occurring, obtained via recombinant DNA technology, or a biologically active derivative thereof. As used herein, "endogenous FVIII" includes FVIII which originates from a mammal intended to receive treatment. The term also includes FVIII transcribed from a transgene or any other foreign DNA present in the mammal. As used herein, "exogenous FVIII" or therapeutic plasma protein includes clotting factor FVIII that does not originate from a mammal.

The FVIII molecule exists naturally and in therapeutic preparations as a heterogeneous distribution of polypeptides arising from a single gene product. The term "clotting factor VIII" as used herein refers to all such polypeptides, whether derived from blood plasma or produced through the use of recombinant DNA techniques and includes, but is not limited to FVIII mimetics, fc-FVIII conjugates, FVIII chemically modified with water soluble polymers, and other forms or derivatives of FVIII. Commercially available examples of therapeutic preparations containing FVIII include those sold under the trade names of ADVATE, HEMOFIL M, and RECOMBINATE (available from Shire, Bannockburn, Ill., U.S.A.). Other preparations comprise primarily a single subpopulation of FVIII molecules, which lack the B domain portion of the molecule.

The FVIII molecules useful for the present disclosure include a full-length protein, precursors of the protein, biologically active or functional subunits or fragments of the protein, and/or functional derivatives thereof, as well as variants thereof as described herein below. Reference to clotting factor FVIII is meant to include all potential forms of such proteins and wherein each of the forms of FVIII has at least a portion or all of the native B domain sequence intact.

"Dosing interval," as used herein, means an amount of time that elapses between multiple doses being administered to a patient. The dosing interval for administering a therapeutic plasma protein including clotting factor VIII may be at least about every one, two, three, four, five, six, seven, eight, nine, ten, eleven, twelve, thirteen, or fourteen days or longer. The dosing interval may change based on changing conditions/characteristics of a patient, changes to a minimally acceptable (e.g., target trough) concentration of the therapeutic plasma protein within a patient, and/or changes to a dosage.

FIG. 1 illustrates an example pharmacokinetic (PK) environment 100 in which a drug monitoring tool 150 operates, according to an example embodiment of the present disclosure. The environment 100 includes a remote server 120 that includes a model generator 125, QR generator 132, and PK server 130. The remote server 120 is communicatively coupled to a data store 115 that stores patent medical samples 110.

The model generator 125 is configured to generate one or more patient pharmacokinetic (PK) models based upon sampled patient data 110. The environment 100 also includes a pharmacokinetic ("PK") server 130 that is configured to provide patients, healthcare providers, and/or sales representatives with a graphical pharmacokinetic drug dosing tool 150 based upon the one or more pharmacokinetic models. In the illustrated embodiment, the PK server 130 transmits the patient PK model to the drug monitoring tool 150 via a network 114 (e.g., an Internet). In other embodiments, the PK server 130 hosts the PK profile, which is accessible by the drug monitoring tool 150. In these other embodiments, the PK server 130 may include a single server, or alternatively, may be distributed within a cloud computing framework.

The example PK server 130 and/or the model generator 125 may be communicatively coupled to a database 115 configured to store the patient pharmacokinetic (PK) models. The database 115 may include any type of computer-readable medium, including RAM, ROM, flash memory, magnetic or optical disks, optical memory, or other storage medium. The example database 115 may also store information generated in response to users using the tool 150 including, for example, patient information, dosing regimes, etc. In some instances, the database 115 may be managed by a separate third-party storage provider.

In some instances, the PK server 130 and/or the model generator 125 may be provided by the same server (e.g., the remote server 120) and/or processor and/or operated by the same entity. In these instances, the functionality of the model generator 125 may operate in conjunction with the functionality of the PK server 130. For instance, the model generator 125 may periodically update pharmacokinetic models with therapeutic plasma protein dosing information and/or patient information received in the PK server 130 via the tool 150.

In some example embodiments, a pharmacokinetic (PK) model is used to approximate pharmacokinetic (PK) profiles of patients. For instance, current methods to determine a patient-specific pharmacokinetic profile for hemophilia A include performing multiple blood tests. These blood tests include performing an initial blood draw to determine a clotting factor VIII baseline in a patient. Then, after therapeutic plasma protein is administered, five or more blood draws are performed over a 48-hour post-infusion period. As can be appreciated, such a procedure is especially taxing on a patient, healthcare provider, and lab because of the numerous separate blood draws. Accordingly, the example model generator 125 is configured to generate relatively accurate pharmacokinetic models based upon a sample of patients with varying ages, body weights, genders, and activity levels. These models are then used to determine or approximate a pharmacokinetic profile of a patient without having to subject a patient to all of the blood draws and subsequent analysis.

In an embodiment, the PK models are determined using patient samples 110 selected from one or more sets of patient data. The patient samples 110 may be, for example, selected among patients who have already been subscribed a therapeutic dosing regimen using the above described blood draw procedure. The patient samples 110 may also include patients specifically selected to go through the blood draw procedure for the purpose of creating the models. The patient samples 110 may include patients from one hospital or medical system and/or patients associated from multiple hospitals, medical systems, geographic regions, etc.

The patient samples 110 include data for patients of varying ages, body weights (or body mass index ("BMI"), medical conditions, clinical laboratory data, genders, and/or activity levels. In the example described herein, sample patient ages vary between 2 and 100 years of age. In some embodiments, the data for the patients may be separated into children and adult age brackets such that a separate model is generated for each bracket. The patient data may additionally or alternatively be partitioned based on weight, gender, and/or activity level.

As mentioned, the example patient samples 110 include a determination of clotting factor VIII before therapeutic plasma protein is infused into the patients. Then, post infusion blood samples are collected from each patient after certain durations of time. It should be appreciated that in other examples, the blood samples may be collected at different times and/or the number of blood samples collected may be fewer or greater. For instance, fewer blood samples may be collected from children.

The example model generator 125 creates a PK patient model by performing a Bayesian analysis that uses previous knowledge of clotting factor VIII in the sampled patients over time after an infusion of the therapeutic plasma protein. In some instances, the model generator 125 is configured to analyze each patient's sampled dosing history in conjunction with pre-infusion clotting factor VIII levels, so that washout data is not needed to construct the PK models. In other embodiments, the model generator 125 may use patient washout data in conjunction with the post-infusion clotting factor VIII levels to create one or more pharmacokinetic models. Patient washout data corresponds to a baseline where the patient does not include the therapeutic plasma protein in their system.

The example model generator 125 creates the one or more PK models using, for example, the patient sample data. The model generator 125 may combine the individual patient samples 110 into one or more population profiles (e.g., age sets, weight sets, activity level sets, endogenous clotting factor VIII level, etc.), which is then used as a basis for the respective pharmacokinetic model. For instance, the model generator 125 may group the patient samples 110 for different ages, weights, and/or activity levels into different sets. The model generator 125 then performs covariate and statistical modeling on the grouped patient samples 110 of each set to create a population pharmacokinetic model for that set, as described in a white paper titled "Population pharmacokinetics of recombinant factor VIII—the relationships of pharmacokinetics to age and body weight", by Bjorkman et al., the entirety of which is incorporated herein by reference. It should be appreciated however, that the model generator 125 may model the sampled data 110 using other Bayesian analysis techniques (e.g., a naive Bayes classifier).

In the illustrated example, the covariate model used by the model generator 125 determines relationships between pharmacokinetic parameters (e.g., how quickly therapeutic plasma protein is metabolized, endogenous clotting factor VIII level, etc.) and patient characteristics (e.g., age, body weight, clinical laboratory data, gender, activity level, etc.). The model generator 125 uses a statistical model to determine variance in pharmacokinetic parameters among the sampled patients in addition to residual variance as a result of biological variability between patients, measurement errors, and errors within the fit of the sampled data 110 to the pharmacokinetic model.

The example model generator 125 is configured to perform the covariate and statistical modeling using non-linear mixed effects modeling with a first-order integral approximation method, as provided in SAS® software (NLMIXED procedure). In the illustrated example, the model generator 125 uses a two-compartment model. In other examples, the model generator 125 may use a single compartment model or three or more compartment models. In the illustrated two-compartment example, the first compartment includes pharmacokinetic parameters of clearance ("CL") and volume of distribution (V1). CL refers to the amount of time for a patient to metabolize the therapeutic plasma protein in milliliters ("mL") per hour per kilogram ("kg"). In other words, clearance is a measure of efficiency and rate at which a therapeutic plasma protein is removed or eliminated from a patient.

Responsive to creating one or more pharmacokinetic models, the model generator 125 provides the pharmacokinetic model(s) to the PK server 130. The transmission may be over a private network, such as a local area network, or over a public network, such as an Internet. The model generator 125 may also store the models to the database 115, which is also accessible by the PK server 130 via one or more interfaces. In other instances, the model generator 125 may be integrated with the PK server 130.

The example model generator 125 may refine the models for each patient. For instance, the PK server 130 may receive patient specific information including, weight, age, gender, endogenous clotting factor VIII level, and dosing level for previous treatments. The model generator 125 uses the previous treatment information (e.g., dosing amounts, intervals, etc.) to refine or adjust the model such that dosing recommendations and a pharmacokinetic profile are more aligned to the specific patient but still account for potential patient variance. The model generator 125 transmits the patient-specific model to the PK server 130.

Alternatively, the PK server 130 may be configured to create patient-specific models using the pharmacokinetic model provided by the model generator 125 to account for the patient-specific pharmacokinetic variance. In this manner, one or more base models are refined or adjusted by the PK server 130 responsive to receiving previous treatment information for a specific patient. The PK server 130 may be configured to store the patient-specific model to the database 115 for subsequent uses by the same healthcare provider or other healthcare providers.

Once a PK profile for a patient is generated, the PK server is configured to transmit the PK profile to the drug monitoring tool 150. In some embodiments, the PK server 130 can encrypt the data file prior to transmission. The encryption can be specific to a particular patient such that the drug monitoring tool 150 can only open and process a received PK profile if the tool 150 has a patient specific authentication key.

In other embodiments, the PK server 130 can provide the PK profile to the QR generator 132. The QR generator 132 can generate a quick response (QR) code that can be scanned by the drug monitoring tool 150 via scanner 160. The QR code can also be encrypted using known or yet to be known methods of encrypting QR codes. In some examples, the QR code encryption is specific to the patient for which the PK profile was generated. Accordingly, a drug monitoring tool 150 can only scan and process the QR code if the drug monitoring tool 150 includes appropriate security key(s) and decryption logic. Particularly, the QR code can be presented to the user of the drug monitoring tool 150. The user then scans the QR code using scanner 160. In some embodiments, the drug monitoring tool includes an activation toolkit 155. The activation toolkit 155 is configured to enable access to functionalities of the drug monitoring tool 150 in response to at least of: receiving the PK profile the patient and/or receiving a log of a first prophylactic infusion.

Once the drug monitoring tool 150 is activated, the tool 150, via processor(s) 165, generates an interactive user interface 175 for display on the tool 150. An example of the user interface 175 is further described herein in reference to, for example, FIG. 5. The user interface 175 is configured to display a graphical representation of a time-varying amount of the therapeutic plasma protein within the patient at any given time. The graphical representation delineating zones associated with the time varying amount of the therapeutic plasma protein. Each zone is associated with a particular concentration range of the time-varying amount of the therapeutic plasma protein within the patient.

The drug monitoring tool 150 can be communicatively coupled to an infusion pump 140 and a biological collector 135. The infusion pump 140 can be configured to automatically administer a particular clotting factor VIII drug based on a dosing 30 regimen/treatment schedule. In some embodiments, the infusion pump 140 can be configured to administer a dose of the particular clotting factor VIII drug in response to results of a biological sample collected by the biological collector 135. For example, the collector 135 can collect a blood sample and determine a factor VIII level of the patients. In response to the amount, the infusion pump 140 can administer a dose of the particular clotting factor VIII drug.

Additionally, the environment 100 can include an ecosystem monitoring system 180 that is coupled to the network 105 and in communication with both the remote server 120 and drug monitoring tool. The system 180 can provide notification to a pharmacist to prepare the particular clotting factor VIII drug for purchase by a patient. For example, the system 180 can determine that the patient has a threshold amount of the drug left such that the patient will be in need of the drug in the near future. Similarly, the system 180 can contact a physician to ensure that physician has real-time information associated with the patient. Accordingly, the physician can take immediate actions to care of the patient if a need arises.

Figure 2:
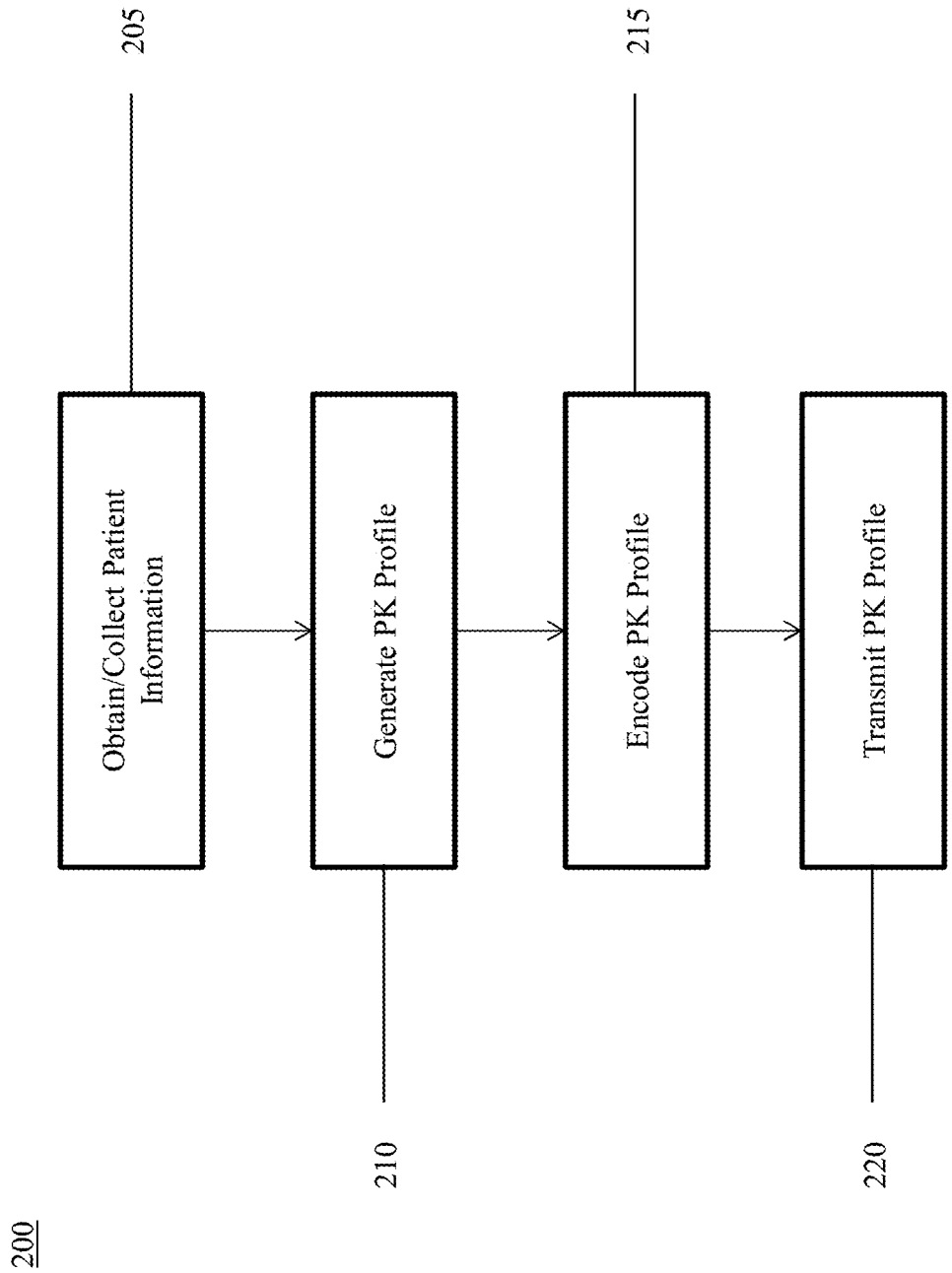
FIG. 2 is a flow diagram of a method for generating a PK profile of a particular patient in accordance with an example embodiment of the present disclosure.

FIG. 2 is a flow diagram of a method 200 for generating a PK profile of a particular patient in accordance with an example embodiment of the present disclosure. The method 200, at 205, includes collecting patient information (e.g., patient sample 110, medical history, etc.). At 210, the method 200 includes generating a PK profile 210 for a patient. The PK profile can be generated as described in U.S. patent application Ser. No. 14/311,133 filed on Jun. 20, 2014 (now published as U.S. Pat. Pub. No. 2014/0379629 on Dec. 25, 2014). The entire teachings of which are incorporated herein by reference. The method 200, at 215, includes encoding the PK profile. In some examples, the PK profile can be encoded by the PK Server 130 using known or yet to be known electronic data encoding techniques. At 220, the method 200 includes transmitting the PK profile to a drug monitoring tool 150.

Figure 3:
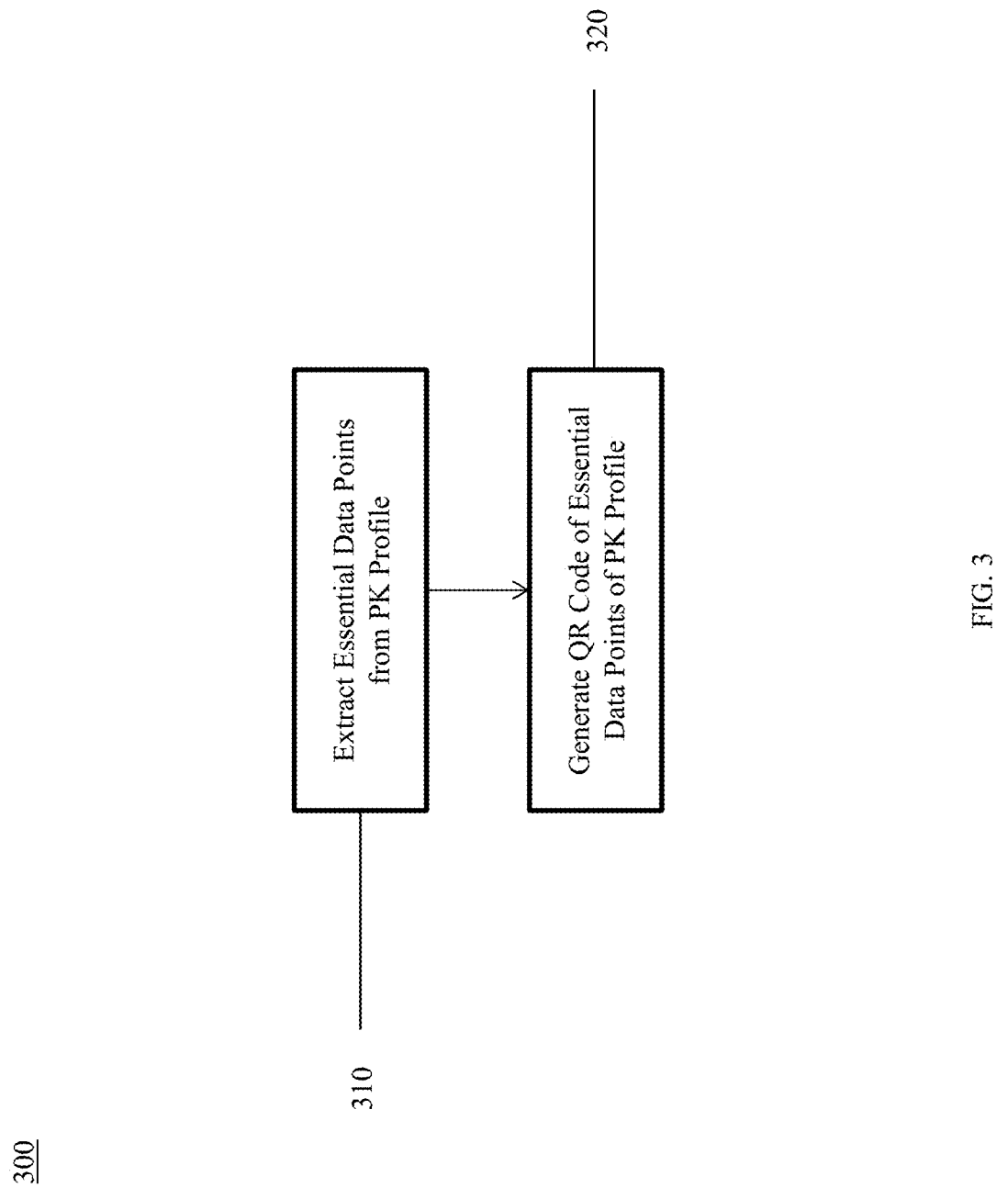
FIG. 3 is a flow diagram of a method for converting a PK profile into a QR code in accordance with an example embodiment of the present disclosure.

FIG. 3 is a flow diagram of a method 300 for converting a PK profile into a QR code in accordance with an example embodiment of the present disclosure. The method 300, at 310, includes extracting essential data points from a PK profile. For example, Table 1 below identifies information that is encoded into the QR code for an example patient:

TABLE 1

| Field Name | Position | Description | Example UTF8 |
|---|---|---|---|
| Schema Version | 0 | Format identifier of message. | 1 |
| Clinic Patient ID | 1 | Patient ID from myPKFiT | 153213465 |
| Weight | 2 | Weight in kilograms | 100.0 |
| Alpha | 3 | Constants for FVIII estimate. | 0.15305152251119972 |
| Beta | 4 | Constants for FVIII estimate. | 0.04031213652124507 |
| K21 | 5 | Constants for FVIII estimate. | 0.12959298505994027 |
| V1 | 6 | Constants for FVIII estimate. | 90.9144113054100 |
| Duration | 7 | Schedule Type enumeration, see below. | Every 2 Days |
| Dosing Interval Mon | 8 | Custom schedule with Monday infusion. 1 implies active. 0 implies inactive. | 0 |
| Dosing Interval Tues | 9 | Custom schedule with Tuesday infusion. 1 implies active. 0 implies inactive. | 1 |
| Dosing Interval Wed | 10 | Custom schedule with Wednesday infusion. 1 implies active. 0 implies inactive. | 0 |
| Dosing Interval Thurs | 11 | Custom schedule with Thursday infusion. 1 implies active. 0 implies inactive. | 1 |

TABLE 1-continued

| Field Name | Position | Description | Example UTF8 |
|---|---|---|---|
| Dosing Interval Fri | 12 | Custom schedule with Friday infusion. 1 implies active. 0 implies inactive. | 0 |
| Dosing Interval Sat | 13 | Custom schedule with Saturday infusion. 1 implies active. 0 implies inactive. | 1 |
| Dosing Interval Sun | 14 | Custom schedule with Sunday infusion. 1 implies active. 0 implies inactive. | 0 |
| FVIII Baseline | 15 | Natural factor VIII baseline for Factor Meter display. | 5.0 |
| Target Trough | 16 | Target trough for Factor Meter display. | 19.1 |
| Time Above | 17 | Time above/green zone threshold for Factor Meter Display. | 79.9 |
| Time Below | 18 | Time below/red zone threshold for Factor Meter Display. | 10.1 |
| Report Timestamp | 19 | Date myPKFiT assessment for report identification. ISO-8601 format. UTC time reference. | 2015 Jan. 27T 04:41:32.0000000Z |

The method 300, at 320, then generates the QR code using information from Table 1 above. The method 300 can generate the QR code to have the patient information encrypted using AES-256 encryption with cipher block chaining (CBC) and public-key cryptography standards (PKCS) padding.

Figure 4:
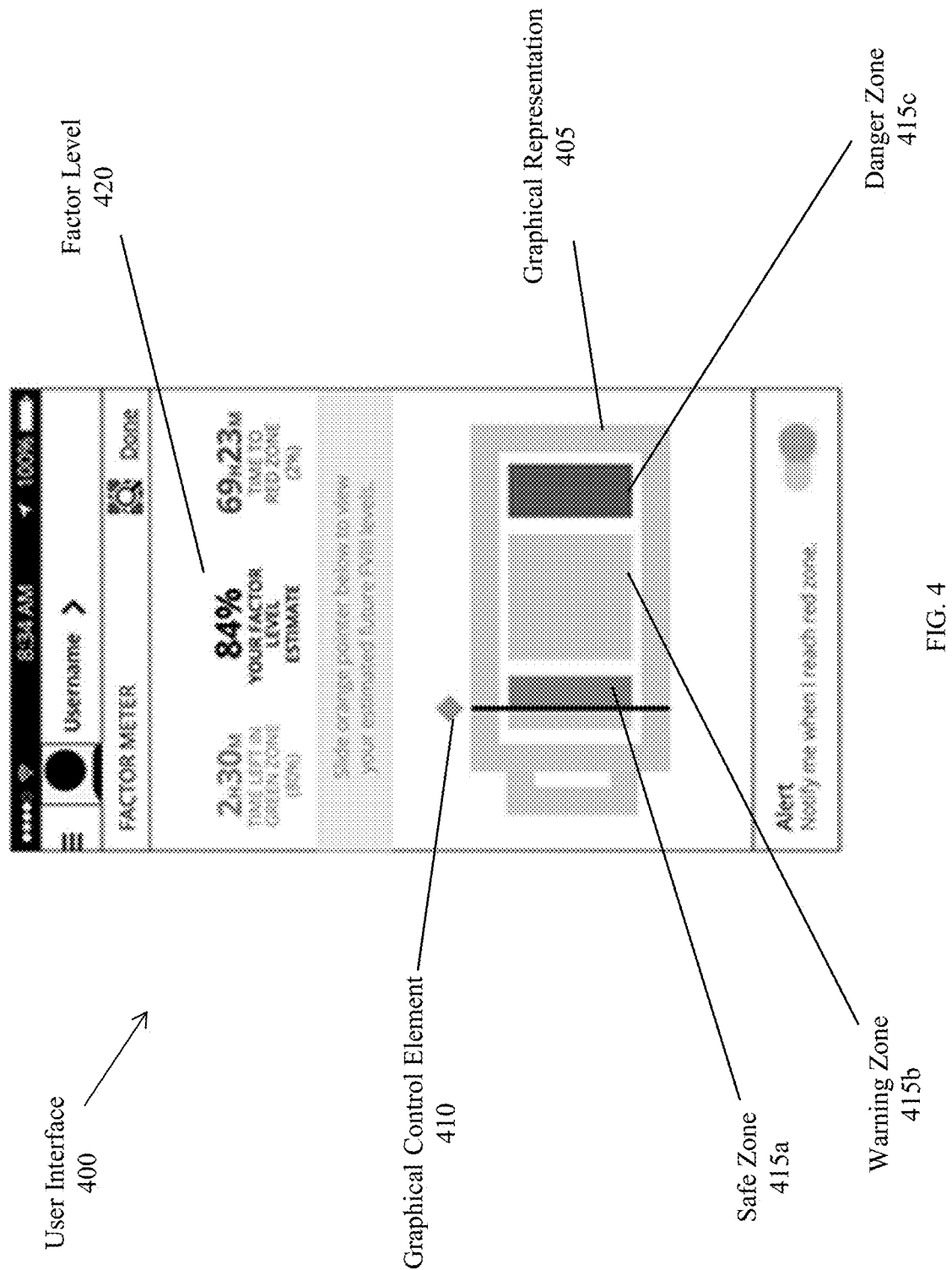
FIG. 4 illustrates an interactive user interface of a drug monitoring tool in accordance with an example embodiment of the present disclosure.

FIG. 4 illustrates an interactive user interface 400 of a drug monitoring tool (e.g., the tool 150 of FIG. 1) in accordance with an example embodiment of the present disclosure. The interactive user interface is configured to display a graphical representation 405 of a time-varying amount of the therapeutic plasma protein within the patient at any given time. In this example, the representation is that of a battery. Those skilled in the art will understand that any representation could be used to convey the time-varying nature of a drug level. The graphical representation 405 delineating zones 415a-c associated with the time varying amount of the therapeutic plasma protein. For example, a safe zone 415a indicates that levels of the clotting factor VIII are considered safe for many anticipated activity levels. A warning zone 415b provides an indication to a patient that they should carefully select an activity level in order to prevent a bleed event. The danger zone 415c indicates that the patient should administer another dose of the particular clotting factor VIII drug in the near future. The danger zone 415c also provides an indication to the patient that activity levels should be kept to a minimum.

The interface 400 also includes a representation of a current drug level (e.g., Factor level) of a drug (e.g., a specific clotting factor VIII drug). The interface 400 further includes a graphical control element 410 configured to receive patient input corresponding to a request for the time-varying amount of the therapeutic plasma protein within the patient at a particular time. In response to a patient sliding the graphical control element 410, the interactive user interface 400 is configured to display the time varying amount of the therapeutic plasma protein within the patient at the particular time corresponding to a position of the graphical control element 410.

Figure 5:
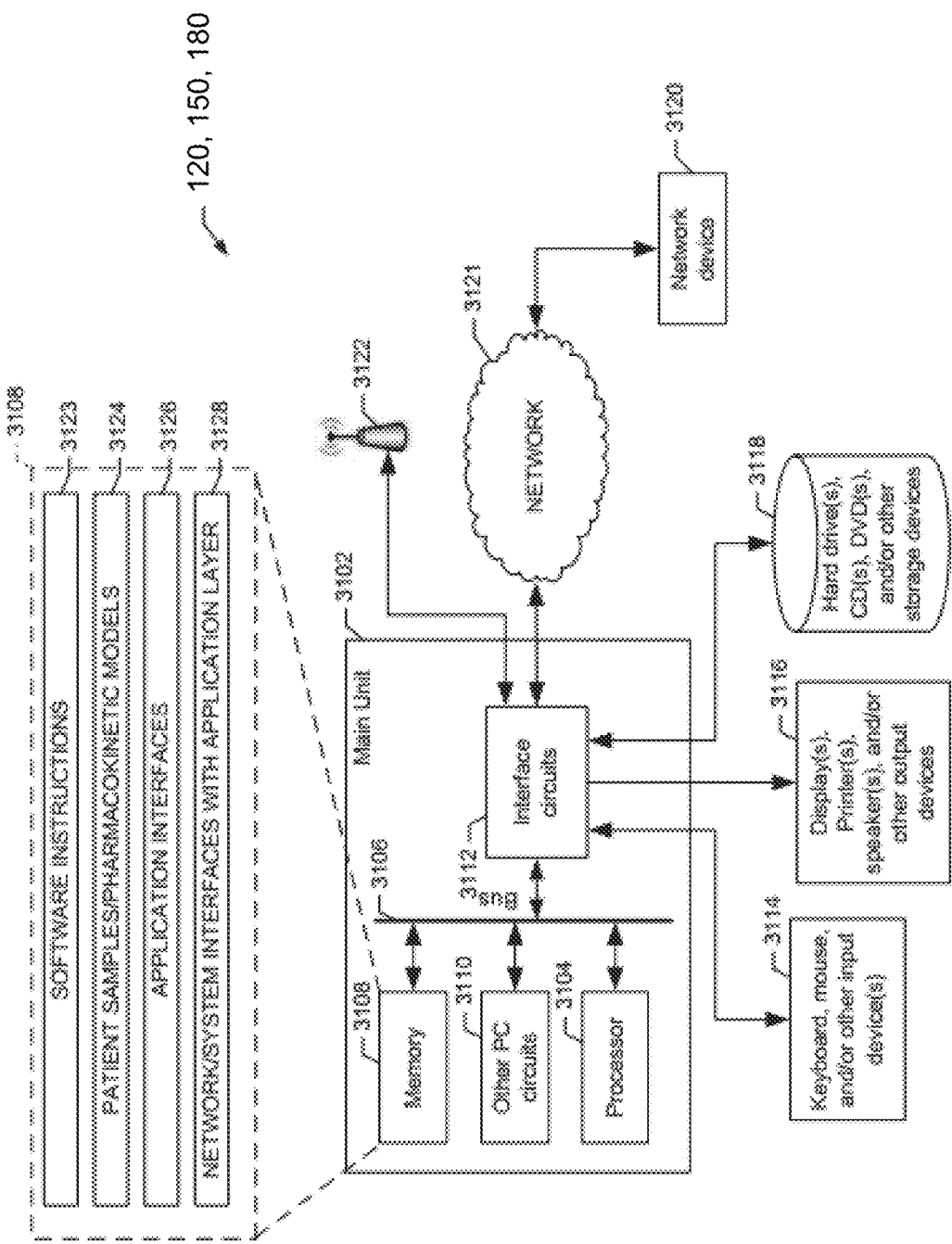
FIG. 5 is a detailed block diagram of an example remote server, drug monitoring tool, and ecosystem monitoring system in accordance with an example embodiment of the present disclosure.

FIG. 5 is a detailed block diagram of an example computing device 3000. The computing device 3000 can be any communication device such as a desktop computer, laptop computer, server system, cloud-based computing system, wireless transmit/receive unit (WTRU) (e.g., smartphone, tablet computer, mobile phone, personal digital assistant (PDA), etc.). Accordingly, the computing device 3000 can be, for example, the remote server 120, drug monitoring tool 150, and/or the ecosystem monitoring system 180.

In this example, the device 3000 includes a main unit 3102. The main unit 3102 preferably includes one or more processors 3104 communicatively coupled by an address/data bus 3106 to one or more memory devices 3108, other computer circuitry 3110, and one or more interface circuits 3112. The processor 3104 may be any suitable processor, such as a microprocessor from the INTEL PENTIUM® or CORE® family of microprocessors. The memory 3108 preferably includes volatile memory and nonvolatile memory. Preferably, the memory 3108 stores a software program that interacts with the other devices in the environment 100, as described above. This program may be executed by the processor 3104 in any suitable manner. In an example embodiment, memory 3108 may be part of a "cloud" such that cloud computing may be utilized by the device 3000. The memory 3108 may also store digital data indicative of documents, files, programs, webpages, patient samples, pharmacokinetic models, patient pharmacokinetic profiles, etc. retrieved from (or loaded via) the device 3000.

The example memory devices 3108 store software instructions 3123, patient samples/pharmacokinetic models 3124, application interfaces 3126, user interface features, permissions, protocols, identification codes, content information, registration information, event information, and/or configurations. The memory devices 3108 also may store network or system interface features, permissions, protocols, configuration, and/or preference information 3128 for use by the device 3000. It will be appreciated that many other data fields and records may be stored in the memory device 3108 to facilitate implementation of the methods and apparatus disclosed herein. In addition, it will be appreciated that any type of suitable data structure (e.g., a flat file data structure, a relational database, a tree data structure, etc.) may be used to facilitate implementation of the methods and apparatus disclosed herein.

The interface circuit 3112 may be implemented using any suitable interface standard, such as an Ethernet interface and/or a Universal Serial Bus (USB) interface. One or more input devices 3114 may be connected to the interface circuit 3112 for entering data and commands into the main unit 3102. For example, the input device 3114 may be a keyboard, mouse, touch screen, track pad, track ball, isopoint, image sensor, character recognition, barcode scanner, microphone, and/or a speech or voice recognition system.

One or more displays, printers, speakers, and/or other output devices 3116 may also be connected to the main unit 3102 via the interface circuit 3112. The display may be a cathode ray tube (CRTs), a liquid crystal display (LCD), or any other type of display. The display generates visual displays generated during operation of the device 3000. For example, the display may provide a user interface and may display one or more webpages received from the device 3000. A user interface may include prompts for human input from a user of the device 3000 including links, buttons, tabs, checkboxes, thumbnails, text fields, drop down boxes, etc., and may provide various outputs in response to the user inputs, such as text, still images, videos, audio, and animations.

One or more storage devices 3118 may also be connected to the main unit 3102 via the interface circuit 3112. For example, a hard drive, CD drive, DVD drive, and/or other storage devices may be connected to the main unit 3102. The storage devices 3118 may store any type of data, such as identifiers, identification codes, registration information, patient samples, patient information, pharmacokinetic models, patient pharmacokinetic profiles, treatment regimes, statistical data, security data, etc., which may be used by the device 3000.

The computing device 3000 may also exchange data with other network devices 3120 via a connection to a network 3121 (e.g., the Internet) or a wireless transceiver 3122 connected to the network 3121. Network devices 3120 may include one or more servers, which may be used to store certain types of data, and particularly large volumes of data which may be stored in one or more data repository. A server may process or manage any kind of data including databases, programs, files, libraries, identifiers, identification codes, registration information, content information, patient samples, patient information, pharmacokinetic models, patient pharmacokinetic profiles, treatment regimes, statistical data, security data, etc. A server may store and operate various applications relating to receiving, transmitting, processing, and storing the large volumes of data. It should be appreciated that various configurations of one or more servers may be used to support, maintain, or implement the device 3000 of the environment 100. For example, servers may be operated by various different entities, including operators of the PK server 108, hospital systems, patients, drug manufacturers, service providers, etc. Also, certain data may be stored in the device 3000 which is also stored on a server, either temporarily or permanently, for example in memory 3108 or storage device 3118. The network connection may be any type of network connection, such as an Ethernet connection, digital subscriber line (DSL), telephone line, coaxial cable, wireless connection, etc.

Access to the device 3000 can be controlled by appropriate security software or security measures. An individual third-party client or consumer's access can be defined by the device 3000 and limited to certain data and/or actions. Accordingly, users of the environment 100 may be required to register with the computing device 3000.

While this disclosure has been particularly shown and described with references to example embodiments thereof, it will be understood by those skilled in the art that various changes in form and details may be made therein without departing from the scope of the present disclosure encompassed by the appended claims.

What is claimed is:

1. A drug monitoring tool that enables a patient to view a personalized real-time indication of clotting factor VIII levels following a prophylactic infusion event, the tool comprising:
    a data receiver configured to receive a pharmacokinetic (PK) profile of a patient for clotting factor VIII based on (i) a Bayesian model of PK profiles of sampled patients having received an infusion of clotting factor VIII and (ii) at least one of a bodyweight, a von Willebrand factor ("vWF") level, and/or an age of the patient; and
    an interactive user interface configured to:
        display to the patient a graphical representation of a time-varying therapeutic plasma protein level of the patient based on an administered dose of a clotting factor VIII and the PK profile of the patient;
        delineate a plurality of zones within the graphical representation associated with the time-varying therapeutic plasma protein level, wherein each zone is associated with a particular concentration range of clotting factor VIII within the patient and based on the PK profile, the plurality of zones comprising at least:
            a safe zone indicating to the patient that the time-varying therapeutic plasma protein level of clotting factor VIII for the patient is within a first concentration range above an upper threshold that is considered safe for physical activity; and
            a danger zone indicating to the patient that the time-varying therapeutic plasma protein level of clotting factor VIII for the patient is within a second concentration range below a lower threshold and physical activity should be limited.

2. The drug monitoring tool of claim 1, further comprising an activation toolkit configured to enable access to functionalities of the drug monitoring tool in response to at least one of: receiving the PK profile the patient and/or receiving a log of a first prophylactic infusion.

3. The drug monitoring tool of claim 1, wherein the interactive user interface includes a graphical control element configured to receive patient input corresponding to a request for the time-varying therapeutic plasma protein level at a particular time, and wherein the interactive user interface is configured to display the graphical representation of the time-varying therapeutic plasma protein level within the patient at the particular time.

4. The drug monitoring tool of claim 3, wherein the graphical control element is slidable between the plurality of zones.

5. The drug monitoring tool of claim 1, wherein:
the data receiver is a camera configured to scan a quick response (QR) code storing patient information that includes at least PK profile information; and
the drug monitoring tool further comprising a QR code processor configured to extract and process the PK profile of the patient.

6. The drug monitoring tool of claim 5, further comprising a QR code generator configured to generate the QR code having patient information encrypted using AES-256 encryption with cipher block chaining (CBC) and public-key cryptography standards (PKCS) padding.

* * * * *